(12) United States Patent
Schoenfuss et al.

(10) Patent No.: US 10,161,871 B2
(45) Date of Patent: Dec. 25, 2018

(54) CHEMICALLY STABLE SENSING UNIT WITH PROTECTOR ELEMENT

(71) Applicant: HAMILTON Bonaduz AG, Bonaduz (CH)

(72) Inventors: Dirk Schoenfuss, Tamins (CH); Claudius-Michael Ortega Schulte, Domat/Ems (CH)

(73) Assignee: HAMILTON BONADUZ AG, Bonaduz (CH)

( * ) Notice: Subject to any disclaimer, the term of this patent is extended or adjusted under 35 U.S.C. 154(b) by 649 days.

(21) Appl. No.: 14/410,772

(22) PCT Filed: Nov. 27, 2013

(86) PCT No.: PCT/EP2013/074795
§ 371 (c)(1),
(2) Date: Dec. 23, 2014

(87) PCT Pub. No.: WO2014/083020
PCT Pub. Date: Jun. 5, 2014

(65) Prior Publication Data
US 2015/0192519 A1   Jul. 9, 2015

(30) Foreign Application Priority Data

Nov. 30, 2012 (DE) .......... 10 2012 111 686

(51) Int. Cl.
*G01N 21/64* (2006.01)
*G01N 21/76* (2006.01)
(Continued)

(52) U.S. Cl.
CPC ......... *G01N 21/6428* (2013.01); *G01N 21/76* (2013.01); *G01N 21/78* (2013.01);
(Continued)

(58) Field of Classification Search
CPC .... G01N 21/6428; G01N 21/76; G01N 21/78; G01N 31/225; G01N 2201/062;
(Continued)

(56) References Cited

U.S. PATENT DOCUMENTS 4,195,056 A   3/1980 Patel
4,271,121 A   6/1981 Diller et al.
(Continued)

FOREIGN PATENT DOCUMENTS

DE   32 41 992 A1   7/1983
DE   32 13 661 A1   10/1983
(Continued)

OTHER PUBLICATIONS

Opitz N et al: "Single molecule FCS-based oxygen sensor (O2-FCSensor): a new intrinsically calibrated oxygen sensor utilizing fluorescense correlation spectroscopy (FCS) with Single fluorescent molecule detection sensitivity", Sensors and Actuators B; Chemical, vol. 96, No. 1-2, Nov. 15, 2003, pp. 460-467.
(Continued)

*Primary Examiner* — Que Tan Le
*Assistant Examiner* — Jennifer D Bennett
(74) *Attorney, Agent, or Firm* — McCormick, Paulding & Huber LLP (57) ABSTRACT

The invention relates to a sensing unit (1) comprising a housing (2) that has a first housing opening which can be oriented towards a medium (M) to be analyzed, and a second housing opening on which at least one means for detachably rigidly connecting to a sensor shaft or sensor housing are arranged, or may be arranged, on the inner and/or outer side; at least one sensor element (3) that is arranged in the housing (2) and comprises indicators and, optionally, indicator protectors, said sensor element (3) having a first side facing the first housing opening and a second side lying opposite the
(Continued)

first housing opening; and at least one protector element (4) which is arranged in the region of the first housing opening between the at least one sensor element (3) and the medium (M) which surrounds the sensing unit (1), particularly in the region of said housing opening, such that the sensor element (3) does not come into direct contact with the medium (M).

20 Claims, 4 Drawing Sheets

(51) Int. Cl.
*G01N 21/77* (2006.01)
*G01N 21/78* (2006.01)
*G01N 31/22* (2006.01)

(52) U.S. Cl.
CPC ... *G01N 31/225* (2013.01); *G01N 2021/6432* (2013.01); *G01N 2021/6434* (2013.01); *G01N 2021/775* (2013.01); *G01N 2021/7796* (2013.01); *G01N 2201/062* (2013.01)

(58) Field of Classification Search
CPC ... G01N 2021/6432; G01N 2021/6434; G01N 2021/775; G01N 2021/7796
USPC ....... 250/458.1, 216, 226; 422/52, 400, 425, 422/82.06, 82.07, 82.08
See application file for complete search history.

(56) References Cited

U.S. PATENT DOCUMENTS

| | | | |
|---|---|---|---|
| 4,272,353 A | | 6/1981 | Lawrance et al. |
| 4,272,480 A | | 6/1981 | Stull et al. |
| 4,303,076 A | * | 12/1981 | Danek .................. G01N 27/404 204/403.06 |
| 4,478,792 A | | 10/1984 | McConnaughey et al. |
| 4,526,752 A | | 7/1985 | Perlman et al. |
| 4,748,930 A | | 6/1988 | Leichnitz |
| 4,919,891 A | | 4/1990 | Yafuso et al. |
| 5,143,066 A | * | 9/1992 | Komives ............ G01N 21/6428 250/364 |
| 5,173,432 A | | 12/1992 | Lefkowitz et al. |
| 5,864,397 A | * | 1/1999 | Vo-Dinh ................... G01J 3/44 356/301 |
| 5,985,475 A | * | 11/1999 | Reynolds ............. B01D 53/228 428/422 |
| 6,254,829 B1 | | 7/2001 | Hartmann et al. |
| 6,653,148 B2 | | 11/2003 | Trapp et al. |
| 8,779,388 B2 | | 7/2014 | Wuenn et al. |
| 8,809,765 B2 | | 8/2014 | Weisshaar et al. |
| 2001/0034479 A1 | * | 10/2001 | Ring .................. A61B 5/14556 600/322 |
| 2005/0098032 A1 | * | 5/2005 | Tsai ................... B01D 19/0031 95/46 |
| 2008/0247906 A1 | | 10/2008 | Heffels et al. |
| 2010/0277740 A1 | | 11/2010 | Hulteen et al. |

FOREIGN PATENT DOCUMENTS

| | | |
|---|---|---|
| DE | 3900191 A1 | 7/1990 |
| DE | 43 03 861 A1 | 8/1994 |
| DE | 100 51 220 A1 | 4/2002 |
| DE | 69911062 | 7/2004 |
| DE | 10 2004 033 303 A1 | 11/2005 |
| DE | 69921199 | 2/2006 |
| DE | 10 2005 056 118 A1 | 5/2007 |
| DE | 10 2008 019 889 A1 | 12/2009 |
| DE | 10 2009 003 971 A1 | 7/2010 |
| DE | 10 2009 056 417 A1 | 6/2011 |
| EP | 0 010 160 A1 | 9/1979 |
| EP | 0231086 A2 | 8/1987 |
| EP | 0 638 802 A1 | 7/1994 |
| EP | 1 757 924 A2 | 2/1998 |
| WO | 96/17012 | 6/1996 |
| WO | 02/46740 | 6/2002 |
| WO | 02/056023 A1 | 7/2002 |

OTHER PUBLICATIONS

International Preliminary Report on Patentability for PCT/EP2013/074795 dated Jul. 2, 2015.

German Search Report for DE 10 2012 111 686.5 dated Oct. 17, 2013.

"Single molecule FCS-based oxygen sensor (O2-FCSensor): a new intrinsically calibrated oxygen sensor utilizing fluorescence correlation spectroscopy (FSC) with singe fluorescent molecule detection sensitivity", Science Direct; www.sciencedirect.com; N. Opitz, P.J. Rothwell, B. Oeke, P. Schwille; pp. 460-467.

International Search Report for PCT/EP2013/074795 dated Feb. 28, 2014.

Office Action for European Patent Application No. 13 807 948.8 dated Mar. 15, 2015.

\* cited by examiner

CHEMICALLY STABLE SENSING UNIT WITH PROTECTOR ELEMENT

BACKGROUND

Technical Field

The invention relates to a sensing unit with at least one sensor element, the matrix and sensor connections (indicators) of which are protected from damaging or inactivating influences such as highly reactive compounds by means of at least one other protector element arranged on the media side. The invention further relates to a sensor comprising a sensing unit of this type and to the use of the sensing unit and the sensor for detecting an analyte in an environment that is aggressive for the sensor element.

Discussion of Art

Sensor assemblies are generally known, the measurement principle of which is based on the fact that the sensory-active compounds (indicators) arranged in the sensor or in its sensory element are converted to an excited energy state by the supply of excitation energy. When they release energy, e.g., in the form of light of a certain wavelength, the indicators switch to a lower energy level.

The determination of an analyte in a sample is usually performed by measuring the energy emitted by the indicators, which are sufficiently changed upon contact with an analyte to permit detection.

Different sensor types can be distinguished based on the form of the excitation and emission energy. The indicators of optical sensors, for example, can be excited by the supply of light or chemical or electrical energy, while in each case the emission takes place in the form of light of a definite wavelength. In purely optical sensors, the excitation and emission of the indicators occurs in each case in the form of light of a specific excitation wavelength (v1) and emission wavelength (v2). Optical sensors are used, for example, to determine oxygen, halide ions, heavy metal ions, carbon dioxide ($CO_2$), and the pH value. Here, the sensor principle is based on the characteristic of the indicators to change their optical properties upon contact with the analyte to be determined. The analyte can be detected, for example, by measuring the change of wavelength, the intensity of the emitted light or the luminescence quenching, the change of the luminescence decay time, or the relaxation time of the excited states of the indicator molecules, the phase shift between modulated excitation light and emitted light, and/or the absorption of light waves.

The sensory element of known optical sensors includes at least one sensor element, in or on which the indicators are arranged, such that the indicators are mostly immobilized or incorporated at the surface of the sensor element facing toward the medium being examined. The matrix material of the sensor element is made, for example, from polymer compounds, which may be doped with the indicators.

Sensor elements are generally designed as membranes. Furthermore, state-of-the-art optical sensors generally include a carrier element, which serves as a substrate for the sensor element and may be designed to be transparent to the excitation and/or emission light of the indicators. To achieve high measuring sensitivity, materials with a high transparency such as clear transparent plastics, clear glass or glass fibers are used for the carrier element. Optical sensors also generally include a measuring technique that permits the optical detection of the above-mentioned changes in the optical indicators due to interaction with the analyte being detected. For the measurement it is generally necessary to transmit light through the carrier element to the indicator molecules and to receive it from these again.

At present, sensors are used for the optical measurement of dissolved oxygen which contain luminescence indicators, the luminescence of which is excited by light irradiation of a specific wavelength v1, has itself a wavelength v2, and is dynamically quenched in the presence of oxygen, and the excited state of the luminescence indicator is deactivated in a radiationless manner by oxygen.

Optical sensors are widely used for the reliable determination of an analyte such as molecular oxygen in complex media, because the measurement methods used here are relatively simple and entail low equipment costs. However, conventional optical sensors have the disadvantage that their sensor elements do not provide adequate or long-lasting protection of the indicators they contain from destructive influences, in particular from reactive compounds in the environment being analyzed or from high temperatures. The service life of known sensor elements is therefore especially limited when the individual sensor components, in particular the indicators, are exposed to conditions under which they are permanently and irreversibly damaged or inactivated.

In various applications, the medium to be analyzed contains, for example, compounds which can destroy the indicators due to a chemical reaction, if they are not adequately protected. Thus, the problem with the current state of the technology is that optical sensor elements currently available for determining molecular oxygen either cannot be used or only with a very limited service life, if the medium to be analyzed, such as waste water or water from swimming pools, contains strong oxidants such as ozone, superoxides, or hydroxyl radicals or chlorine or peroxide compounds used for disinfection, the diffusion of which to the indicators in the sensor element cannot be prevented, and contact with them leads to the oxidative inactivation of the indicators. Due to a lack of protection or inadequate protection of the indicators, conventional sensor elements are either not suitable or only to a very limited degree under these conditions.

Optical sensors are still used in areas where methods of analysis must be performed under sterile conditions. Such areas include in particular medicine, the food industry, and biotechnology, which primarily use disposable systems at present. A particular challenge is to provide (optical) sensing units or (optical) sensors which can be sterilized, especially heat-sterilized, because it is above all (optical) sensors which can be heat-sterilized, for example steam-sterilized, which would have economic and ecological advantages over disposable systems, due to their reusability in the sterile environment. However, the optical sensors currently known from the prior art cannot be exposed to the conditions of heat sterilization or only to a very limited extent, since their structure and especially the connectivity of the individual components would be damaged under such conditions, as a result of which sensitive elements of the sensor would be exposed to a destructive environment and the correct functioning of the sensor would thus no longer be ensured.

Heat-sterilizable sensors have to meet special requirements. In particular, the sensor element, including indicators and a (polymeric) matrix for immobilizing them, must be composed in such a way that permeability to the analyte and transparency to the excitation light and the luminescent light is sufficiently retained even after the application of heat during sterilization (e.g. autoclaving). The decisive factor for achieving this is the thermal resistance of the materials used. In addition, the structure, in particular the arrangement and connection of the individual sensor elements in the sensor is essential for the provision of temperature-stable sensors. Therefore it is does not help that the matrix of the sensor element is selected from a heat-stable polymer, if during the sterilization process the sensor suffers mechanical damage, for example, which prevents its continued use according to its intended purpose.

In the optical sensors currently used in process measurement technology, it was found that the indicators they contain are no longer adequately protected against chemical attack, particularly after thermal loads such as those occurring in the course of cleaning and sterilization processes, e.g. during autoclaving, during CIP (Clean in Place) and SIP (Sterilize in Place) treatments. Damage to the indicator-bearing elements mainly occurs when certain substances are present in the liquid process medium and/or cleaning agent, which on reuse of the once heat-sterilized sensor can penetrate its polymeric indicator-bearing sensor element membrane. This is due, on the one hand, to the matrix membrane polymer used for the sensor elements and, on the other hand, to the construction or design of the sensor. The latter can be damaged, for example, due to the influence of heat during the cleaning or sterilization process, which results is the passage of aggressive substances through to the sensing element.

There is therefore a need for sensors or sensing units, in particular optical sensors or sensing units for the luminescence detection of analytes in complex media, the sensor components of which, and in particular the luminescence indicators, are effectively protected against destructive or inactivating influences such as reactive chemicals. This type of sensor or sensing unit should preferably be sterilizable, and especially heat-sterilizable.

Optical sensors whose sensor element matrix consists of thermally stable polymers, are known, e.g., from WO2009016236A1. Mentioned here are those polymers that have a non-aromatic backbone chain, i.e., cyclic olefin polymers or cyclic olefin copolymers such as ethylene-norbornene copolymer, poly (n-methyl methacrylimide) or mixtures of these. A disadvantage of this solution is that the number of matrix polymers, already restricted due to the measuring principles applicable to optical sensors, is further restricted here. As a result, among other things, the luminescence response of a luminescence indicator is strongly dependent on the polymer matrix used. The previously used electronics and firmware of known sensors would have to be adapted to new parameters corresponding to these polymers.

A similar solution proposal for improving the chemical stability of the sensor element membrane of optical sensors is disclosed in EP 1199556B1. This reveals a fluoropolymer as the matrix polymer. In a matrix containing fluoropolymers, as explained in detail in this document, only certain transition metal complexes with special, at least partially fluorinated, ligands, may be employed as luminescent indicators, which severely restricts the application range of the sensors. For example, compounds which are commercially available as oxygen luminescence indicators and commonly used, e.g. platinum porphyrin complexes, cannot be used in a matrix of this type.

It is known from CH 677151 and EP 0478720B1 that films, foils, or membranes made from fluoropolymers, particularly PTFE, can be used to increase the chemical stability of a downstream layer or membrane of an electrochemical or amperometric sensor.

Optical sensors, especially optical sensors for oxygen analysis, the indicator-bearing sensor elements of which are protected against the attack of reactive compounds even after sterilization, thus permitting the long-lasting determination of the analyte by means of luminescence measurement in a (chemical) environment that is aggressive for the indicators, are not known from the prior art, nor can they be derived from it.

BRIEF SUMMARY OF INVENTION

The object of the invention is to provide a sensing unit, in particular a sensing unit for use in optical sensors, which can be used repeatedly for determining an analyte in a chemically aggressive environment and/or is characterized by a longer service life compared to known sensing units. A particular object of the invention was to provide a sensing unit, whose sensor element itself and in particular the indicators arranged in or on the sensing element are protected from direct contact with destructive and/or deactivating substances even after sterilization of the sensing unit, in particular following heat-sterilization, such that their sensory properties, particularly selectivity, measurement range, measurement accuracy, and response time are not affected or only marginally affected without causing harm to the application.

BRIEF DESCRIPTION OF DRAWINGS

The construction and operation of exemplary embodiments of the invention will be better understood with reference to appended drawing figures, among which.

Among the drawings figures, like-numbered parts in different drawings should be understood to be alike, except for any differences specifically shown or described.

DETAILED DESCRIPTION OF EMBODIMENTS

To solve this problem, the present invention provides a sensing unit (1), comprising a) a housing (2) that has a first side or housing opening (2A), which can be oriented to the medium (M) being analyzed, and a second side or housing opening (2B); b) at least one sensor element (3) which is arranged in the housing (2) and comprises indicators and optional indicator protectors, such that the sensor element (3) comprises a first side (3A) facing toward the first housing opening (2A) and/or toward the medium (M) and a second side (3B) situated opposite the first housing opening (2A) and/or facing away from the medium (M); c) and at least one protector element (4).

According to the invention, the protector element (4) is arranged in the area of the first housing opening (2A) between the at-least-one sensor element (3) and the medium (M) which surrounds the sensing unit (1), and in particular in the area around the housing opening (2A), in such a way that the sensor element (3), and in particular its indicator-bearing area or section, cannot come into direct contact with the medium (M).

The housing (2) of the sensing unit (1) is made of a material that is suitable for the individual application. Housings made from metal or metal alloy are appropriate for numerous applications. Preferable in the medical, food chemistry, and biotechnology sectors are, for example, stainless steel alloys, which is why the housing (2) of the sensing unit (1) according to the invention preferably consists of a stainless steel alloy. Furthermore, one embodiment provides a housing that comprises plastic, ceramic, and/or glass, optionally in combination with metal.

At least one means of detachably rigidly connecting the sensing unit (1) to a sensor shaft or sensor housing (8) can be located on the housing (2) in the area of the second housing opening (2B). The fastening means are appropriately arranged on the outside and/or on the interior of the housing (2) and are selected from a screw and/or a plug-in or snap-in mechanism.

If the sensor shaft or sensor housing features a corresponding mechanism, the sensing unit (1) can be screwed, fitted, or latched to the sensor shaft or sensor housing, for example using a bayonet lock or the like. The connection between the sensing unit (1) and the sensor shaft or sensor housing (8) is preferably a media-tight connection. For this purpose, it is possible to include a sealing mechanism, such as O-rings or the like, in the connection. Alternatively, the sensing unit (1) and the sensor shaft or sensor housing are integrated in a common housing and/or the sensing unit (1) is an integral part and functional section of a sensor.

Furthermore, the sensing unit (1) can be permanently fixed to a shaft sensor or sensor housing (8), for example glued, welded, or soldered. As regards the spatial design, the sensing unit (1) according to the invention is preferably cap-shaped, tube-shaped or sleeve-shaped. It is particularly preferred that the sensing unit (1) is cap-shaped (sensor cap).

It can be advantageous if the sensing unit (1) according to the invention, in addition to the above-mentioned components (2) to (4), further comprises a carrying element (5), on which or upstream of which the sensor element (3) is arranged on the medium side, i.e., such that the second side (3B) of the sensor element (3) contacts the carrier element (5). The sensor element (3) and the carrier element (5) are preferably arranged such that the second side (3B) of the sensor element is in full-surface contact with the carrier element (5) on its medium-facing side, i.e. the entire surface of the side (3B) is lying directly on the carrier element (5). The area between the sensor element (3) and the carrier element (5) is preferably cavity-free. Alternatively, one embodiment provides that the sensor element (3) forms a single unit with the carrier element (5), which may have different functional sections.

As the sensing element (3), the sensing unit (1) according to the invention preferably contains an optical sensor element comprising indicators selected from the same or different luminescence-active agents (luminescence indicators). It is further provided that the sensor element (3) and the carrier element (5), or the unit formed by the sensor element (3) and carrier element (5), is transparent to emission light and/or excitation light from the luminescent indicators. The carrier element (5) is preferably made from clear glass, clear plastic, or optical fibers, or comprises these materials. If the carrier element (5) and the sensor element (3) form a unit, then the matrix is preferably made from clear glass, clear plastic, or glass fibers, or comprises these materials. Suitable materials with transparent properties are known to the specialist. The sensor element (3) is advantageously coupled, via the (transparent) support element (5), to an optical system, which, depending on the intended use, can be arranged partially or completely in the sensing unit (1) and/or in a sensor housing (8) with which the sensing unit can be connected. The optical system can be a system known to specialists in the field, comprising a detection unit or measuring unit for detecting or measuring the emission, such as a photodetector or photodiode, an evaluation unit, and a means of exciting the luminescence of the indicators—for example, a light source, such as a light-emitting diode, if photoluminescence indicators are used.

In the context of the present invention, the term "optical sensor element" refers to sensor elements which contain luminescence indicators. Luminescent indicators are molecules, compounds, or substances that have the property of emitting light of a definite wavelength (luminesce) following excitation by a certain amount of energy. In addition, luminescence indicators have the property that, in the presence of a particular compound or substance or group of compounds or substances, their luminescence is characteristically altered with respect to intensity, duration, and/or wavelength. Substances that characteristically alter the luminescence of indicators that are selective for them can be determined quantitatively and/or qualitatively, depending on sensor construction and method of measurement, as an analyte by measuring the change(s) to the luminescence. In principle, all luminescence indicators known to specialists in the field can be used in the sensor element according to the invention. Suitable luminescent indicators include, for example, chemiluminescence, electro(chemi)luminescence, thermoluminescence, radio luminescence, sonoluminescence, photoluminescence indicators and combinations of these. Primarily photoluminescence indicators, i.e., fluorescent and/or phosphorescent indicators, are stipulated for use in the sensing unit (1) according to the invention. Furthermore, it is intended to use luminescence indicators, the luminescence emission of which is selectively quenched upon contact with at least one analyte. In one embodiment, the sensor element (3) comprises luminescence indicators, and in particular photoluminescence indicators, whose luminescence emissions are selectively quenched upon contact with oxygen, and preferably with molecular oxygen. Particularly preferred are indicators the luminescence emissions of which are dynamically quenched in the presence of oxygen, such that the excited state of the luminescence indicators undergoes radiationless deactivation upon contact with oxygen. Luminescence indicators that are particularly suitable for the determination of oxygen include the complexes ruthenium, rhenium, rhodium, iridium, lanthanide, as well as metallated porphyrins (e.g. platinum and/or palladium porphyrins) and unmetallated porphyrins, or mixtures of these, optionally in combination with fluorinated dyes and/or light stabilizers.

The sensor element (3) is preferably designed as a single-layered or multi-layered, for example, two-, three-, four-, five- or six-layered membrane, on the side (3A) of which facing towards the medium (M) the indicators are arranged, e.g. doped. The sensor element preferably also includes indicator protectors. If the sensor element membrane (3) has a multi-layered structure, the indicator protectors can be situated in one layer (indicator protector-bearing layer) and the indicators can be arranged in a different layer of the element (3) (indicator-bearing layer). The indicator protector-bearing layer is preferably located upstream from the indicator-bearing layer on the media side. In the case of a membrane-like design, the sensor element (3) has a thickness of between 0.001 and 1 mm, preferably between 0.005 and 0.5 mm, and more preferably between 0.01 and 0.2 mm.

The matrix material of the sensor element (3) comprises or preferably consists of a polymer or polymer mixture, selected from polystyrene, polyvinyl chloride, polyalkyl-methacrylate, especially polymethyl-methacrylate, poly-isobutylmethacrylate, and poly-2-hydroxyethyl-methacrylate, poly-α-methylstyrene, silica gels, sol-gels, hydrogels, polyurethanes, polytetrahydrofurans, polytetrafluoroethylene, polyester, polybutadiene, polyvinyl butyral, polyethyl acrylate, ethyl cellulose, cellulose triacetate, cellulose acetylbutyrat, polysulfones, polysulfides, silicones, fluorinated silicones, and combinations of these, optionally in combination with plasticizers. Indicator protectors according to the present invention are agents which protect the luminescence indicators from destruction or inactivation due to external influences. The protection of the indicators is achieved by the inactivation, neutralization, and/or adsorptive immobilization of compounds and/or by the inactivation, neutralization, or insulation of energy-rich radiation, which has an inactivating and/or destructive, especially oxidizing, effect on the indicators.

Suitable as indicator protector(s) are reactants of one or more compounds or substances, which have a destructive or deactivating effect on the indicators upon contact with them. The reactants react with the destructive/inactivating compounds or substances, for example, in a chemical reaction to at least one product that is harmless to the indicators. In this context the term "indicator protector(s)" is not limited to reactants, which are converted, upon reaction with the compound or substance that destroys or deactivates the indicator, to at least one new compound that is not or less destructive/inactivating for the indicator. The term "indicator protector(s)" also covers agents that have a catalytic effect (catalyst), which catalyze the conversion of the indicator destroying/inactivating compound or substance to at least one new compound that is not or less destructive/inactivating for the indicator. In this context, in addition to a purely catalytic effect, the term "catalyst" or "agents with a catalytic effect" also refers to compounds that also have a simple chemical reactivity in the sense of a reactant that is itself converted as part of the reaction.

Also suitable as indicator protector(s) are adsorbents of one or more compounds or substances that act on the indicators in a destructive or deactivating manner upon contact with them. Adsorbents completely or partially inhibit the diffusion of the indicator-destroying or indicator-inactivating compound or substance in the direction of the indicators.

Also particularly suitable as indicator protectors are combinations of the above-mentioned reactants, catalysts, and/or adsorbents. It is also possible that the agents used as indicator protectors can act either as reactant, catalyst, and/or adsorbent. The protector element (4) is preferably arranged on the sensor element (3), or on the unit comprising the sensor element and carrier element, in such a way that the protector element (4) is in immediate or direct contact with the first side (3A) of the sensor element (3). It is particularly preferred that the entire surface, or at least the entire surface of the side of the sensor element (3) containing the indicators (3A), is immediately or directly contacted by the side of the protector element (4) facing away from the medium (M). Most preferably, the side of the protector element (4) facing away from the medium (M) is located upstream of or resting on the entire surface, or at least the entire indicator-bearing surface, of the side (3a) of the sensor element (3) that faces towards the medium (M). The area between the sensor element (3) and the protector element (4) is preferably cavity-free.

In a particularly preferred embodiment, the sensor element (3) is in (full-surface) contact with the protector element (4) on side (3A) and with the carrier element (5) on side (3B), while the arrangement of the individual elements in relation to each other is as above described. The protector element (4) preferably comprises one or more fluoropolymers, or consists of these. Suitable fluoropolymers are known to the specialist in the field. Polytetrafluoroethylene polymers (PTFE) are particularly suitable, since they are chemically inert to many reactive compounds. The protector element (4) is preferably designed as a one-layered or multi-layered membrane (protector element membrane). It is particularly preferred that the protector element (4) is a single-layered or multi-layered protector element membrane comprising or consisting of PTFE.

The thickness of the protector element (4) in the sensing unit (1) according to the invention is 1 to 100 µm, preferably 10 to 100 µm, and more preferably 20 to 50 µm. The protector element (4) must be sufficiently permeable to the analyte being determined. The layer thickness and material of the protector element should be selected according to the intended application for the sensory unit, and here it should be ensured that the response time of the sensor is not adversely affected.

The response time of optical sensors, unlike that of amperometric sensors, for example, is not dependent on the formation of a diffusion gradient in the sensory layer, to which the measured current is proportional, but rather from the setting speed of the thermodynamic phase equilibrium of the analyte, between the medium (M) and of the indicator-bearing phase (3).

It is therefore particularly preferred that the permeability of the protector element (4) to the specific analyte being determined, both in the operating state as well as before and after heat sterilization (e.g. thermal autoclaving), is greater than or at least equal to the corresponding permeability of the sensor element (3). The protector element (4) preferably acts as a barrier for non-analytes, and in particular for compounds that are harmful to the sensor element (3); that is, the protector element prevents direct contact between such compounds and the sensor element (3). Harmful compounds include reactive lyophilic or organophilic substances which penetrate into the sensor element matrix and can destroy it. Further harmful compounds are substances such as chlorine, ozone, hydroxyl radicals, peroxide radicals, and/or superoxides, which have an inactivating and/or destructive effect on the indicators, for example, by means of oxidative and/or free radical attacks.

The protector element (4) is preferably gas-permeable. It is particularly preferred that the protector element (4) is (selectively) permeable to gaseous oxygen, in particular molecular oxygen. In particular, the protector element (4) has a gas permeability to oxygen of at least $5 \times 10-9$ cm2 s−1 mmHg−1 or $3,750 \cdot 10-15$ m4 s−1 N−1.

The gas permeability of the protector element (4) is preferably greater than the corresponding gas permeability of the sensor element (3).

In a preferred embodiment, the protector element (4) is gas-permeable and impermeable to non-gaseous compounds.

A problem that arose during the development of the sensory unit was that protector elements (4) in the form of fluoropolymers, and in particular of fluoropolymer membranes such as PTFE membranes as described above, turned out to be difficult to combine with other materials. Initial attempts to connect the protector element (4), in particular a protector element (4) in the form of a fluoropolymer membrane, to the housing (2) and/or to the sensor element (3) and/or to the carrier element (5) by means of bonding failed. Bonding was only possible when the surface of the fluoropolymer membrane was chemically functionalized, for example, by etching. However this requires a highly complicated process. Moreover, it can adversely affect the properties of the fluoropolymer membrane in terms of its permeability to the analyte(s). In addition, a further barrier to the analyte is created by the adhesive itself.

Another object of the invention was therefore to provide a sensory unit (1) as described above, in which a protector element (4) as described above, e.g., in the form of a fluoropolymer membrane, is connected to the housing (2) and/or to the sensor element (3) and/or to the carrier element (5) and/or to the unit consisting of the sensor element (3) and the carrier element (5) in a permanent and, optionally, in a thermostable manner. The use of adhesive in the production of this compound should be avoided.

It was a particular object of the invention, to provide a sensory unit (1) as described above, in which the joint between the protector element (4) and the housing (2) and/or the sensor element (3) and/or support element (5) and/or the unit consisting of the sensor element (3) and the carrier element (5) is gas-tight, and uses a simple compound; that is, it should be created without the use of a prior complicated process, such as the prior functionalization of the protector element (4).

This object was achieved by providing a sensing unit (1) as described above, in which the protector element (4) in the area of the first housing opening (2A) is mechanically connected, i.e., without the use of adhesive and without welding, to the housing (2) and/or to the sensor element (3) and/or to the carrier element (5) and/or to the unit consisting of the sensor element (3) and the carrier element (5) in a permanent or detachable manner, such that, in a preferred embodiment, the mechanical connection is impermeable at the joint to components of the medium being analyzed (M), and is more preferably gas-tight.

A preferred embodiment provides that the protector member (4) mechanically connected to the housing (2) and/or to the sensor element (3) and/or to the carrier element (5) and/or to the unit consisting of the sensor element (3) and the carrier element (5) is designed as a membrane (protector element membrane) as described above.

In the context of the present invention, the term "mechanical connection" refers to a fixed or detachably fixed connection, whereby the protector member (4) is pressed, at the joint, to the housing (2) and/or to the sensor element (3) and/or to the carrier element (5) and/or to the unit consisting of the sensor element (3) and the carrier element (5), or the said components are pressed, screwed, and/or latched together at the joint. The protector element (4) is preferably pressed, at the joint, to the housing (2) and/or to the sensor element (3) and/or to the carrier element (5) and/or to the unit consisting of the sensor element (3) and the carrier element (5).

To ensure a mechanical connection, one embodiment of the invention specifies the following configuration, without however being restricted to it:

A protector element (4) as described above, in particular a protector element membrane (4), is mechanically fixed to the housing (2) at a folded edge (K) of the housing (2) which is situated in the area of the first housing opening (2A) and oriented to the interior of the housing, such that a peripheral area of the protector element membrane (4) is encompassed or covered by the folded edge of the housing (K). In this embodiment, the peripheral or border area of the protector element membrane (4) is preferably arranged in a groove-shaped element (N) located in the area of the first housing opening (2a), such that the periphery of the membrane (4) in particular is pushed or pressed into such an element (N). The groove-shaped area (N) may be defined by the folded edge (K) on the one hand and by the carrier element (5) and/or the unit consisting of the sensor element (3) and the carrier element (5) on the other. A favorable design solution has been found, in which the groove-shaped element (N) is defined by the folded edge of the housing (K) and a pressing element (P), which is arranged inside the housing and is allocated to the folded edge, in particular a press ring.

In one embodiment, the pressing element (P) can be a molding of the housing (2); that is, the pressing element is here a specifically shaped section of the housing (2), preferably in the lumen bearing section of the housing. In another embodiment, the pressing element (P) is a separate component of the sensing unit (1) and is permanently or detachably connected to the housing (2). It is preferably arranged on the inside of the housing, such that it projects into the housing lumen. In this case, the element (P) can consist of the same material as the housing or a different material. The element (P) is preferably made from a metal alloy and in particular from stainless steel.

It is particularly preferred that the protector element membrane (4) is mechanically connected to the housing (2) and/or to the sensor element (3) and/or to the carrier element (5) and/or to the unit consisting of the sensor element (3) and the carrier element (5), in such a way that the periphery or the border area of the membrane (4) covers the front side of the pressing element (P), in particular press ring, which faces toward the first housing opening (2A), at least so far that a surface area defined by the inner diameter of the pressing element (P), in particular press ring, is completely spanned by the protector element membrane (4).

The mechanical connection within the groove-shaped area (N) is preferably achieved using at least one sealing and/or clamping element, in particular an O-ring (O), which can be inserted into it. The material and dimensions of the sealing and/or clamping element are selected such that, in the inserted state, it exerts a sufficiently high pressing force on the protector element (4) to create a mechanical connection, to ensure that it is securely mechanically connected, or to connect it as described above to the housing (2) and/or to the sensor element (3) and/or to the carrier element (5) and/or to the unit consisting of the sensor element (3) and the carrier element (5).

In a particularly preferred embodiment, the sensor element (3), the protector element (4) and, optionally, the carrier element (5) are pressed together with and into the housing (2) by means of a common pressing element (P), and a sealing and/or clamping element (O) ensures sealing against the medium to be analyzed and the respective elements are as described above.

In this case, the protector element (4) is preferably a membrane as described above, in particular a fluoropolymer membrane. The pressing element (P) is preferably a press ring. The sealing and/or clamping element is preferably an O-ring.

This embodiment may further be designed such that the components of the sensory unit (1) in contact with the medium are limited to the outer surface of the housing (2), the sealing and/or clamping element (O), and the protector element (4). This is achieved, for example, when the diameter of the protector element membrane (4) is equal to or greater than the outer diameter of the O-ring used. It is also advantageous if the diameter of the sensor element (3), in particular the diameter of the indicator-bearing area of the sensor element (3), or the unit consisting of the sensor element (3) and the carrier element (5), is not greater than the inner diameter of the compressed O-ring. In this way, crushing and compression of the sensor element (3) during pressing can be avoided, in particular in its embodiment as a sensor element membrane.

A further design of the sensing unit according to the invention specifies that the pressing element (P) is a press ring as described above, and the carrier element (5) or the unit consisting of the sensor element (3) and the carrier element (5) is integrated in its lumen.

A further design of the sensing unit according to the invention specifies that the sensor element (3) forms a unit with the carrier element (5) and, optionally, with the press ring (P), and the housing (2) and the unit comprising the sensor element (3) and the carrier element (5) and, optionally, the press ring (P) are preferably formed as a single body. A one-piece body of this type can be made, for example, from a plastic material. This plastic material is advantageously selected from the group consisting of thermoplastic plastics, in particular polycarbonate, polyvinylidene fluoride, polyethylene terephthalate, polypropylene, polyvinyl chloride, polystyrene, acrylonitrile-butadiene-styrene, polyamide, polylactate, polymethyl methacrylate, polyethylene, and polyether ether ketone, or mixtures of these.

The plastic material is preferably transparent to the excitation and/or emission light of the indicators.

Another object of the invention was to provide a sensing unit that has no or only the smallest possible gap or cavity between the sensor element (3) and the protector element (4) in order to keep the response time of the sensor low, as the latter depends on the setting speed of the thermodynamic phase equilibrium of the analyte, e.g. oxygen, between the medium (M) and the sensor element (3).

To avoid cavities between the sensor element or the sensor element membrane (3) and the protector element or protector element membrane (4), it is advantageous that the side of the carrier element (5) facing the first housing opening (2A) or the unit consisting of the sensor element (3) and the carrier element (5) has a convex or lens-like shaped and the carrier element or the unit consisting of the sensor element (3) and carrier element (5) is a plano-convex-shaped body. The lens-shaped molding of the carrier element (5), or of the unit consisting of the sensor element (3) and the carrier element (5), which is directed toward the medium side, causes a tensioning of the protector element of the membrane (4) during pressing. Another advantage here is that gas bubbles, which can form on the sensing unit (1) when it is immersed in a liquid medium (M) being analyzed, cannot remain on the front of the protector element membrane (4) or only to a slight degree, i.e. cannot remain stuck on its medium-contacting side, because they are led away by the convex molding, even during vertical immersion into the medium (M). It is also advantageous here that, due to the lens shape, the luminescent light emitted by the indicators of the sensor element (3) is concentrated on a level on the side of the sensory unit (1) facing away from the media, in particular on the level of a (photo-) detection unit which is located here, whereas the excitation light is scattered. In this way, an increase of intensity can be achieved with the same amount of excitation light or comparatively less excitation light is required, because, by comparison with a planar configuration, more luminescence light reaches the detection unit. If less excitation light is required, this reduces the photobleaching effect, and also extends the service life of the sensory unit (1).

A further object of the present invention is a sensor (8) comprising at least one sensory unit (1) as described above.

A further object of the present invention is a use of a sensory unit (1) as described above, or of a sensor (8) comprising such a sensory unit, for the quantitative and/or qualitative determination of at least one analyte in a medium (M), in particular for the detection of molecular oxygen in a gaseous or liquid medium and/or for the determination of the molecular oxygen content of a gaseous or liquid medium, wherein the medium (M) can contain compounds, such as chlorine, ozone, hydroxyl radicals, peroxide radicals and/or superoxides, which act on the indicators in an inactivating and/or destructive, in particular oxidizing, manner.

The protector element (4) already provides effective protection of the indicators against inactivating and/or destructive compounds, even after heat sterilization, and especially when it is arranged and mechanically secured as described above. Moreover, the protection of the indicators, and thereby the service life of the sensing unit (1) according to the invention, is further increased if the sensor element (3) also includes indicator protectors, as described above, which provide additional protection of the indicators against harmful energy-rich radiation ("photobleaching").

A further object of the present invention is a method of quantitatively and/or qualitatively determining one or more analytes, in particular molecular oxygen, in a medium (M), which involves bringing the medium (M) into contact with a sensing unit (1) as described above, or a sensor (8) comprising such a sensing unit, and the bringing into contact is carried out at the first housing opening (2A).

A further object of the present invention is a kit comprising a sensory unit (1) as described above, or a sensor (8) comprising such a sensory unit. The sensory unit (1) according to the invention is characterized in that it prevents reactive lyophilic or organophilic substances, among other things, from penetrating into the (polymer) matrix of the sensor element (3) and hence prevents the relatively quick destruction of the matrix itself and/or of the indicators by possible oxidative and/or free-radical attacks and the dissolving of the indicators, for example, by means of organic solvents.

Examples of the present invention are represented in FIGS. 1 to 4. The figures show embodiments of the sensory unit (1). However, the present invention is not limited to the embodiments illustrated therein.

Figure 1:
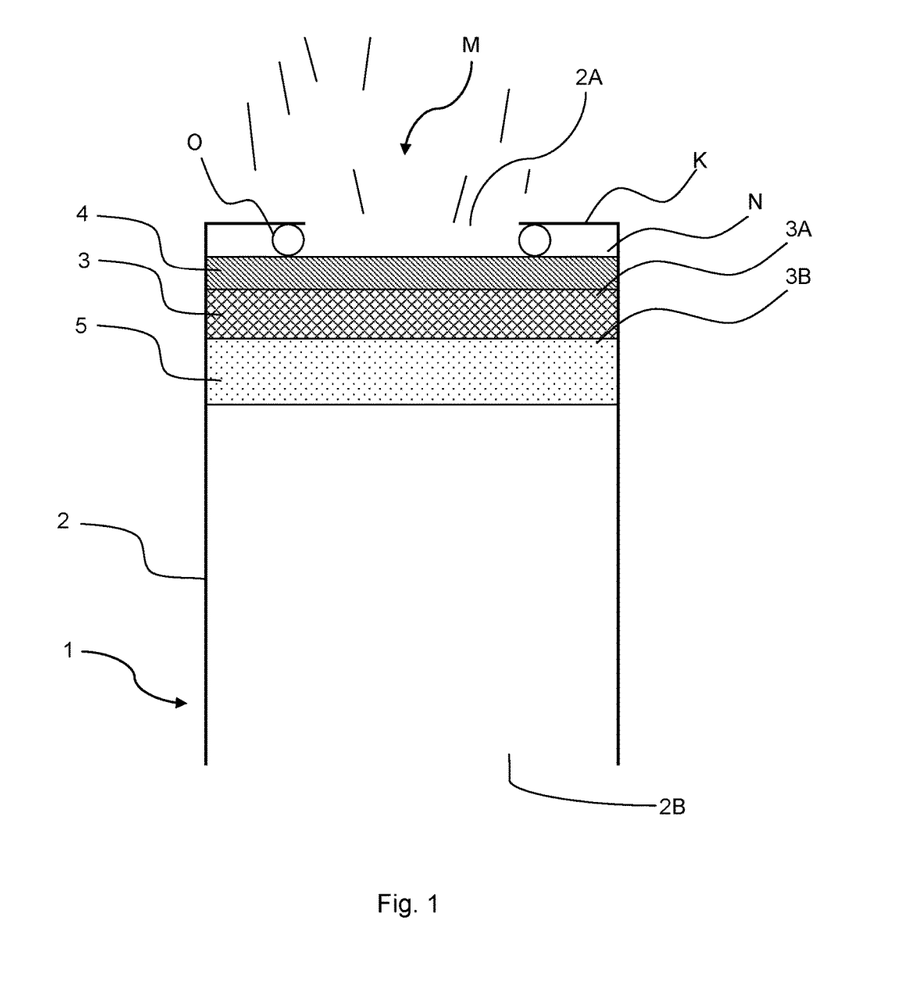
FIG. 1 is a schematic diagram of a sensing unit according to a first embodiment of the invention.

FIG. 1 is a schematic diagram of the sensing unit (1) according to the invention in the form of a sensor cap with a sensor housing (2), on the side (2A) of which facing the medium (M) is situated a folded edge (K) that projects into the interior of the housing or into the housing lumen. The protector element membrane (4) rests without cavities on the side of the sensor element (3) facing towards the media (3A) and covers at least the indicator-bearing surface of the sensor element (3) on side (3A). The side (3B) of the sensor element (3) facing away from the medium (M) rests without cavities on the carrier element (5), which is (detachably) rigidly connected to the inner wall of the housing (2). The carrier element (5) and folded edge (K) define a groove-shaped area (N). The protector element membrane (4) is mechanically connected to the housing (2), and the periphery or edge region of the membrane (4) that projects into the groove-shaped area (N) is pushed or pressed against the side of the carrier element (5) facing the medium by an O-ring (O) which is inserted in the groove-shaped area (N). The sensor element (3) is situated between the protector element membrane (4) and the carrier element (5) in the form of a membrane. Protector element membrane (4) and sensor element membrane (3) have the same diameter, which is why the edge area of the sensor element membrane (3) is also included by the mechanical connection and is also pushed or pressed against the side of the carrier element (5) facing the medium by the O-ring (O) inserted in the groove-shaped area (N).

Figure 2:
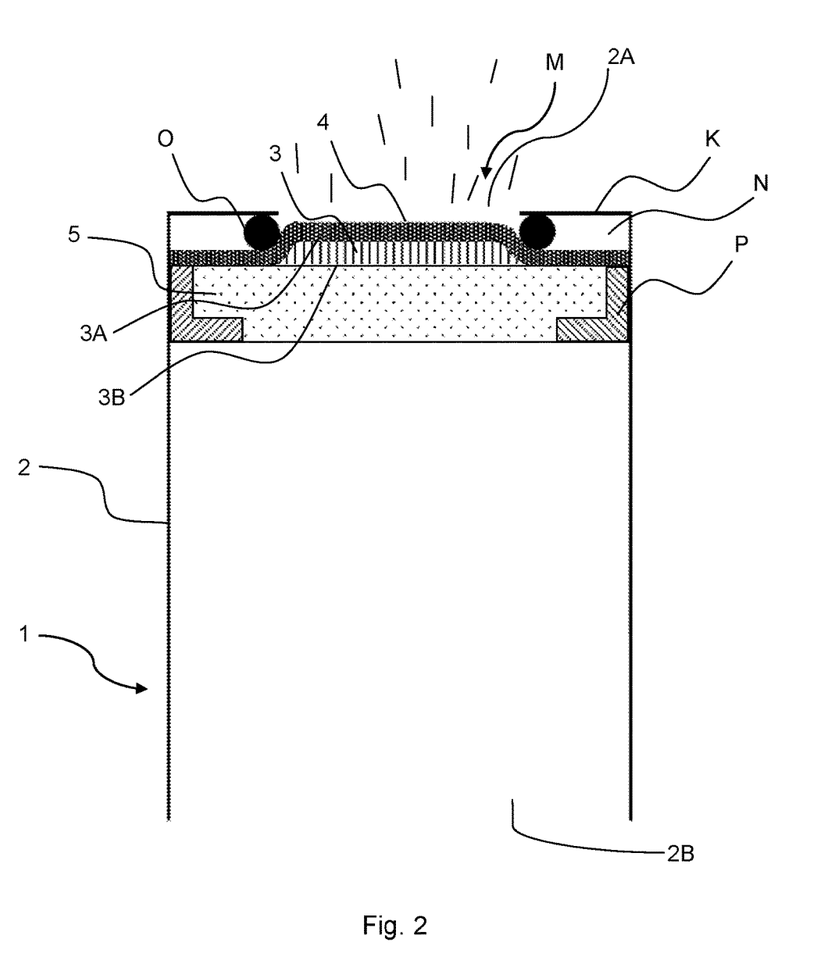
FIG. 2 is a schematic diagram of a sensing unit according to a second embodiment of the invention.

FIG. 2 is a schematic diagram of the sensing unit (1) according to the invention in the form of a sensor cap with a sensor housing (2), on the side (2A) of which facing the medium (M) is situated a folded edge (K) that projects into the interior of the housing or into the housing lumen. There is a pressing ring (P) arranged inside the housing such that the side of it facing the media is situated opposite the folded edge (K) and forms a groove-shaped area (N) with this. The periphery or the edge area of the protector element membrane (4) projects into the groove-shaped area (N), and the periphery or the edge area of the membrane (4) covers the media-side of the press ring (P) so far that the lumen or the surface area defined by the inner diameter of the press ring (P) is spanned by the membrane (4). The membrane (4) rests without cavities on the side of the sensor element (3) facing towards the media (3A) and covers at least the indicator-bearing surface of the sensor element (3) on side (3A). The side (3B) of the sensor element (3) facing away from the medium (M) rests without cavities on the carrier element (5), which is integrated into the lumen of the press ring (P). The protector element membrane (4) is mechanically connected to the housing (2), and the periphery or edge region of the membrane (4) that projects into the groove-shaped area (N) is pushed or pressed against the side of the press ring (P) facing the medium by an O-ring (O) which is inserted in the groove-shaped area (N).

Figure 3:
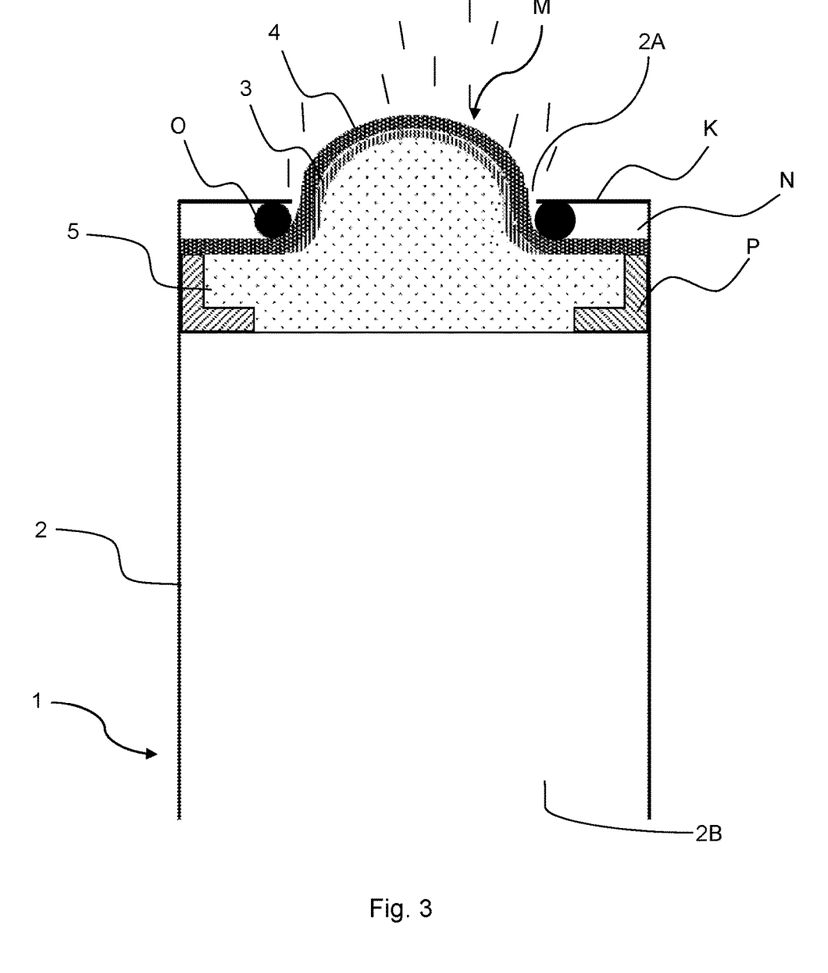
FIG. 3 is a schematic diagram of a sensing unit according to a third embodiment of the invention.

FIG. 3 shows a schematic diagram of the sensing unit (1) according to the invention in the form of a sensor cap, the elements of which are arranged identically to the structure shown in FIG. 2. In contrast to FIG. 2, the carrier element (5) in FIG. 3 has a plano-convex shape, such that the side of the element (5) facing the medium (M) is outwardly convex or lens-shaped, i.e., in the direction of the medium (M), so that the sensor element (3) and protector element membrane (4) rest without cavities on the lens-shape molding.

Figure 4:
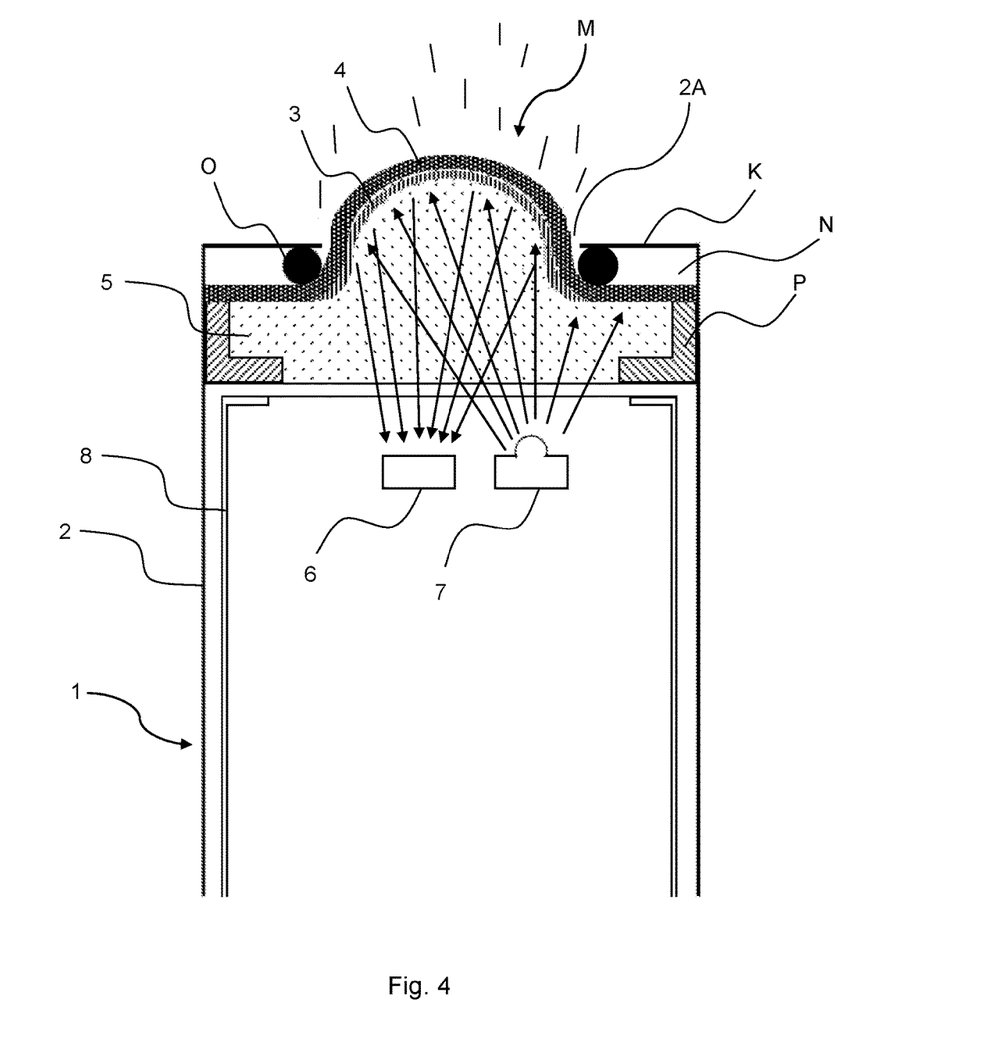
FIG. 4 is a schematic diagram of a sensing unit according to a fourth embodiment of the invention.

FIG. 4 shows a schematic diagram of a sensor area with a sensing unit (1) according to the invention like that shown in FIG. 3. The sensor (8), a section of which is illustrated, has a transparent side, where the sensing unit (1) is arranged, e.g. mounted. In its interior, the sensor (8) further comprises a detection unit (6) (e.g. a photodetector or photodiode) situated on its front side, and an energy source (7) for emitting excitation light (e.g. an LED). The front side of the sensor (8) and the flat side of the plano-convex-shaped carrier element (5) are aligned and may be in direct contact with each other, i.e., the area between them is cavity-free. The arrows in the direction of the sensor element (3) indicate the radiation path of the excitation light, and the arrows in the direction of the detection unit (6) indicate the radiation path of the emission light of the indicators.

What is claimed is:

1. A sensing unit (1) for connecting to a sensor housing, the sensing unit (1) comprising:
   a) a housing (2) that has a first housing opening (2A), which can be oriented towards a medium (M) to be analyzed, and a second housing opening (2B),
   b) at least one sensor element (3) arranged in the housing (2) and comprising indicators, such that the sensor element (3) having a first side (3A) facing toward the first housing opening (2A) and a second side (3b) lying opposite the first housing opening (2A),
   c) at least one protector element (4), and
   d) a carrier element (5), on or at which the sensor element (3) is arranged, such that the second side (3B) of the sensor element (3) contacts the carrier element (5) or makes full-surface or cavity-free contact with the carrier element (5), or the sensor element (3) forms a single unit with the carrier element (5),
   wherein the protector element (4) is arranged in the area of the first housing opening (2A), between the at-least-one sensor element (3) and the medium (M) surrounding the sensing unit (1) in the area of the first housing opening (2A), such that the sensor element (3) does not come into direct contact with the medium (M),
   wherein the protector element (4) is mechanically connected to the housing (2) and to the sensor element (3) and/or the carrier element (5) and/or the unit formed by the sensor element (3) and carrier element (5) on a folded edge (K) of the housing (2), the folded edge (K) being arranged in an area of the first housing opening (2A) and being oriented to the interior of the housing (2), such that the folded edge (K) encompasses or covers a peripheral area of the protector element (4),
   wherein the peripheral area of the protector element (4) is pushed or pressed into a groove-shaped element (N) which is arranged in the area of the first housing opening (2A) and which is defined by the folded edge (K) of the housing (2) and a pressing element (P), which is arranged inside the housing (2) and assigned to the folded edge (K), and wherein the peripheral area of the protector element (4) covers and is in contact with the front surface of the pressing element (P), which faces towards the first housing opening (2A), at least so far that an inner diameter of the pressing element (P) is completely spanned by the protector element (4), and
   wherein a sealing and/or clamping element (O) is inserted in the groove-shaped area (N) and which effects the mechanical connection.

2. The sensing unit as claimed in claim 1, wherein the sensor element (3) is an optical sensor element and the indicators are selected from luminescent active agents and the sensor element (3) and the carrier element (5) or the unit formed by the sensor element (3) and carrier element (5) is transparent to the emission light and/or excitation light of the luminescence indicators.

3. The sensing unit as claimed in claim 1, wherein the sensor element (3) and/or the protector element (4) is/are each designed as a single-layer or multi-layer membrane.

4. The sensing unit as claimed in claim 1, wherein the sensing unit is a cap-shaped, tube-shaped or sleeve-shaped design.

5. The sensing unit as claimed in claim 1, wherein the protector element (4) is arranged on the sensor element (3) such that the protector element (4) directly contacts the first side (3A) of the sensor element (3) or makes direct full-surface contact or cavity-free contact with the sensor element (3).

6. The sensing unit as claimed in claim 1, wherein the mechanical connection is gas-tight at a joint.

7. The sensing unit as claimed in claim 1, wherein the protector element (4) is designed as a membrane.

8. The sensing unit as claimed in claim 1, wherein the carrier element (5), or the unit consisting of the sensor element (3) and the carrier element (5), is integrated into a lumen of the pressing element (P).

9. The sensing unit as claimed in claim 1, wherein the sensor element (3) forms a single unit with the carrier element (5), and the housing (2) and the unit comprising the sensor element (3) and the carrier element (5) are designed as a one-piece body.

10. The sensing unit as claimed in claim 1, wherein the side of the carrier element (5) facing the first housing opening (2A) or the unit comprising the sensor element (3) and carrier element (5) has a convex shape and the carrier element or the unit comprising the sensor element (3) and carrier element (5) is a plano-convex-shaped body.

11. The sensing unit as claimed in claim 1, wherein the diameter of the protector element (4) is equal to or larger than the outer diameter of the sealing element (O), and/or the diameter of the sensor element (3) is smaller than the inner diameter of the sealing element (O).

12. The sensing unit as claimed in claim 1, wherein the protector element (4) comprises fluoropolymers.

13. The sensing unit as claimed in claim 1, wherein the protector element (4) is gas-permeable and impermeable to non-gaseous compounds.

14. The sensing unit as claimed in claim 13, wherein the protector element (4) is permeable to oxygen, and has a gas-permeability of at least $5 \times 10^{-9}$ $cm^2$ $s^{-1}$ and mmHg or $3.750 \times 10^{-15}$ $m^4$ $s^{-1}$ $N^{-1}$ for oxygen, and is impermeable to non-gaseous compounds.

15. The sensing unit as claimed in claim 1, wherein matrix material of the sensor element (3) includes a polymer or polymer mixture, selected from polystyrene, polyvinyl chloride, polyalkyl methacrylate, poly-α-methylstyrene, silica gels, sol-gels, hydrogels, polyurethanes, polytetrahydrofurans, polytetrafluoroethylene, polyester, polybutadiene, polyvinyl butyral, polyethyl acrylate, ethyl cellulose, cellulose triacetate, cellulose acetyl butyrate, polysulfones, polysulfides, silicones, fluorinated silicones and combinations of these.

16. The sensing unit as claimed in claim 1, wherein the indicators are selected from the complexes ruthenium, rhenium, rhodium, iridium and lanthanide, from metallated porphyrins, unmetallated porphyrins, or from mixtures of these.

17. The sensing unit as claimed in claim 1, wherein the pressing element (P) has a ring shape.

18. The sensing unit as claimed in claim 9, wherein the pressing element (P) is of one piece with the housing (2), the sensor element (3) and the carrier element (5).

19. The sensing unit as claimed in claim 1, wherein the sealing element (O) is an O-ring.

20. The sensing unit as claimed in claim 15, wherein the matrix material consists essentially of at least one of polymethylmethacrylate, polyisobutylmethacrylate, and poly-2-hydroxyethyl-methacrylate.

* * * * *

UNITED STATES PATENT AND TRADEMARK OFFICE
CERTIFICATE OF CORRECTION

PATENT NO. : 10,161,871 B2
APPLICATION NO. : 14/410772
DATED : December 25, 2018
INVENTOR(S) : Dirk Schoenfuss et al.

Page 1 of 1

It is certified that error appears in the above-identified patent and that said Letters Patent is hereby corrected as shown below:

In the Claims

In Claim 14, Column 15, Line 17, please replace "mmHg" with --mmHg$^{-1}$--.

Signed and Sealed this
Twelfth Day of February, 2019

Andrei Iancu
*Director of the United States Patent and Trademark Office*